US00PP13211P3

(12) United States Plant Patent
Utecht

(10) Patent No.: US PP13,211 P3
(45) Date of Patent: Nov. 12, 2002

(54) GERANIUM PLANT NAMED 'FISVULK'

(75) Inventor: Angelika Utecht, Montabaur (DE)

(73) Assignee: Florfis AG, Binningen (SE)

( * ) Notice: Subject to any disclaimer, the term of this patent is extended or adjusted under 35 U.S.C. 154(b) by 0 days.

(21) Appl. No.: 09/991,975

(22) Filed: Nov. 26, 2001

(65) Prior Publication Data

US 2002/0088041 P1 Jul. 4, 2002

(51) Int. Cl.[7] ..... A01H 5/00

(52) U.S. Cl. ..... Plt./330

(58) Field of Search ..... Plt./330

*Primary Examiner*—Kent L. Bell
(74) *Attorney, Agent, or Firm*—Foley & Lardner

(57) ABSTRACT

A new and distinct cultivar of geranium plant named 'Fisvulk', as described and illustrated, and particularly characterized by the combined features of orange-red, cup-shaped flowers, semi-spherically shaped umbels, medium-green foliage with distinct zonation, and medium sized, rounded plant habit.

1 Drawing Sheet

BOTANICAL CLASSIFICATION

*Pelargonium zonale.*

VARIETY DENOMINATION

'Fisvulk'.

BACKGROUND OF THE INVENTION

The present invention comprises a new and distinct cultivar of geranium, botanically known as *Pelargonium zonale*, and hereinafter referred to by the cultivar name 'Fisvulk'.

'Fisvulk' is a product of a planned breeding program which had the objective of creating new geranium varieties with scarlet flower color, relatively compact plant habit, and generally suitable for eary sale.

'Fisvulk' originated from a hybridization made by the inventor Angelika Utecht in a controlled breeding program in Galdar, Gran Canaria, Spain, in 1995. The female parent was the commercial, unpatented variety 'Fisnida', characterized by orange-red colored, single-type flowers, large umbels, medium green, zoned foliage, and relatively vigorous growth. The male parent of 'Fisvulk' was the commercial, unpatented variety 'Othello', having orange-red, semi-double flowers, medium green foliage with strong zonation, and compact plant habit.

'Fisvulk' was selected as one flowering plant within the progeny of the stated cross by Angelika Utecht in 1996 in a controlled environment in Galdar, Gran Canaria, Spain. The first act of asexual reproduction of 'Fisvulk' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1997 in Hillscheid, Federal Republic of Germany, and continuing thereafter, has demonstrated that the combination of characteristics as herein disclosed for 'Fisvulk' are firmly fixed and are retained through successive generations of asexual reproduction. The new cultivar reproduces true to type.

'Fisvulk' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisvulk' in combination distinguish this geranium as a new and distinct cultivar:

1. Round, orange-red, semi-double flowers;

2. Medium sized, roughly semi-spherically shaped inflorescence;

3. Relatively large, medium-green leaves with distinct zonation;

4. Medium sized, well branched and uniformly mounded plant habit; and

5. Early to medium spring flowering response.

Of the many commercial cultivars known to the present inventor, the most similar in comparison to 'Fisvulk' is the patented varieties 'Fisgrand' (U.S. Plant Pat. No. 8,760), and the related cultivars 'Fismerk' (U.S. Plant Pat. No. 12,444), and 'Fisfire' (U.S. Plant Pat. No. 12,489).

In comparison to 'Fisgrand', 'Fisvulk' has an almost similar flower color, but shorter peduncles, and more compact, and more evenly shaped plant habit, and more flowers are developed throughout the summer.

In comparison to 'Fismerk', 'Fisvulk' has more open, cup-shaped flowers, while those of 'Fismerk' look double with the inner petals somewhat irregularly arranged. Furthermore, 'Fismerk' has fuller, more than semi-spherically shaped umbels, smaller leaves, and somewhat lower plant habit than 'Fisvulk'.

In comparison to 'Fisfire', 'Fisvulk' has a less intense, a brighter hue of flower color, and not quite so strong zonation of foliage.

In comparison to 'Othello', 'Fisvulk' has larger umbels and a more distinct zonation of the foliage.

BRIEF DESCRIPTION OF THE DRAWING

The accompanying photographic drawing shows typical flower and foliage characteristics of 'Fisvulk' with colors being as true as possible with an illustration of this type.

The drawing shows a flowering pot plant in a 14 cm container.

DETAILED BOTANICAL DESCRIPTION

In the following description color references are made to The Royal Horticultural Society Colour Chart (R.H.S.). The color values were determined indoors from flowering plants growing in a green-house in May 2001, in Hillscheid, Germany. The measurements were taken in Langley, British Columbia, Canada, in early July 2001, 18 weeks after planting of rooted cuttings. The plants were growing in 8 inch containers and had not been pinched.

Inflorescence:
- *Type.*—Umbel.
- *Shape.*—Almost semi-spherical, somewhat flattened.
- *Average diameter.*—120 mm.
- *Average depth.*—72 mm.
- *Peduncle length.*—188 mm.
- *Peduncle color.*—Light green, RHS 144 B, no anthocyanin.
- *Pedicel length.*—29 mm.
- *Pedicel color.*—Mainly light green, RHS 144 B, upper end slightly reddish infused, RHS 179 A (very weak).
- *Number of flowers per umbel.*—About 25–30.

Corolla:
- *Average diameter.*—48 mm.
- *Form.*—Semi-double.
- *Shape.*—Round, weakly cup-shaped.
- *Number of petals.*—8–10.
- *Number of petaloids.*—0–2, narrow, same color as the petals.
- *Shape of petals.*—Obovate, base attenuate, upper end is rounded, margin is entire.
- *Size of petals.*—Upper petals: length 27–29 mm; width 20–22 mm. Lower petals: length: 25–26 mm; width 22–23 mm.
- *Color (general tonality from a distance of three meters)* .—Bright orange-red.
- *Color of upper petals.*—Between RHS 40 A and 43 A.
- *Markings of upper petals.*—Very weak dull red veins, RHS 53 D.
- *Color of lower petals.*—RHS 40 A.
- *Markings of lower petals.*—Absent.
- *Color of lower surface of petals.*—From RHS 40 A to RHS 40 B.
- *Color of sepals.*—Outer surface light green, RHS 143 C; inner surface light green, RHS 144 C.
- *Number of sepals.*—5.
- *Shape of sepals.*—Linear to lanceolate, acute tip, truncate base, surface with very short pubescence, margin entire.
- *Size of sepals.*—10–11 mm long, 4 mm wide for the largest upper sepal, 3 mm for the other sepals.

Bud (just before petals unfold):
- *Shape.*—Elliptical.
- *Color (sepals).*—Green, RHS 144 A.
- *Color (petals).*—RHS 50 A to RHS 50 B.
- *Length.*—19 mm.
- *Width.*—9 mm.

Reproductive organs:
- *Androecium.*—5–7 fertile anthers, filaments white, RHS 155 D, plenty pollen, orange, RHS 33 A.
- *Gynoecium.*—One pistil per flower, style and stigma red, RHS 43 A, 5 to 6-lobed stigma.
- *Fertility/seed set.*—Occasionally a few seeds are developed. Fruit: Oblong, about 6 mm in diameter, with rostrum (beak), total length about 40 mm. Seed: Oblong, 4–5 mm long, brown, RHS 177 B.

Spring flowering response period: In Hillscheid, Germany, in 2000 plants had on average 0.9 flowers opened 8 weeks after planting of rooted cuttings.

Outdoor flower production: Continuously flowering, relatively rich flowering, the flower count in 2000, In Hillscheid, Germany, indicated about 3 inflorescences per plant in mid May.

Durability: Good stability of flower color, very little fading, relatively good resistance to rain and heat.

Lastingness of the individual flower: About 8 days at 18° C., about 18 days for the umbel.

Pest/disease resistance/susceptibility: No observations to date.

Fragrance: None.

PLANT

Foliage:
- *Shape.*—Kidney-shaped to round, with somewhat open, cordate base, and weak lobes.
- *Margin.*—Bicrenated.
- *Texture.*—Upper surface smooth, velvety.
- *Size of leaf.*—93 mm wide, 52 mm long.
- *Color of upper surface.*—Medium green, approximately RHS 137 C.
- *Color of zonation.*—Brown, about RHS 166 A, distinctness medium.
- *Color of lower surface.*—RHS 137 D.
- *Petioles.*—50–60 mm long, 3 mm diameter, light green in color, approximately RHS 143 A to 144 A.

General appearance and form:
- *Stem color.*—Light green, RHS 144 B.
- *Internode length.*—5–15 mm.
- *Branching pattern.*—Average 9.4 branches.
- *Size of plants.*—Height 25.6 cm, width 42.4 cm, as measured from the top of the soil (base of the main stem) to the surface of the foliage canopy, measured without inflorecences.

I claim:

1. A new and distinct cultivar of geranium plant named 'Fisvulk', as described and illustrated herein.

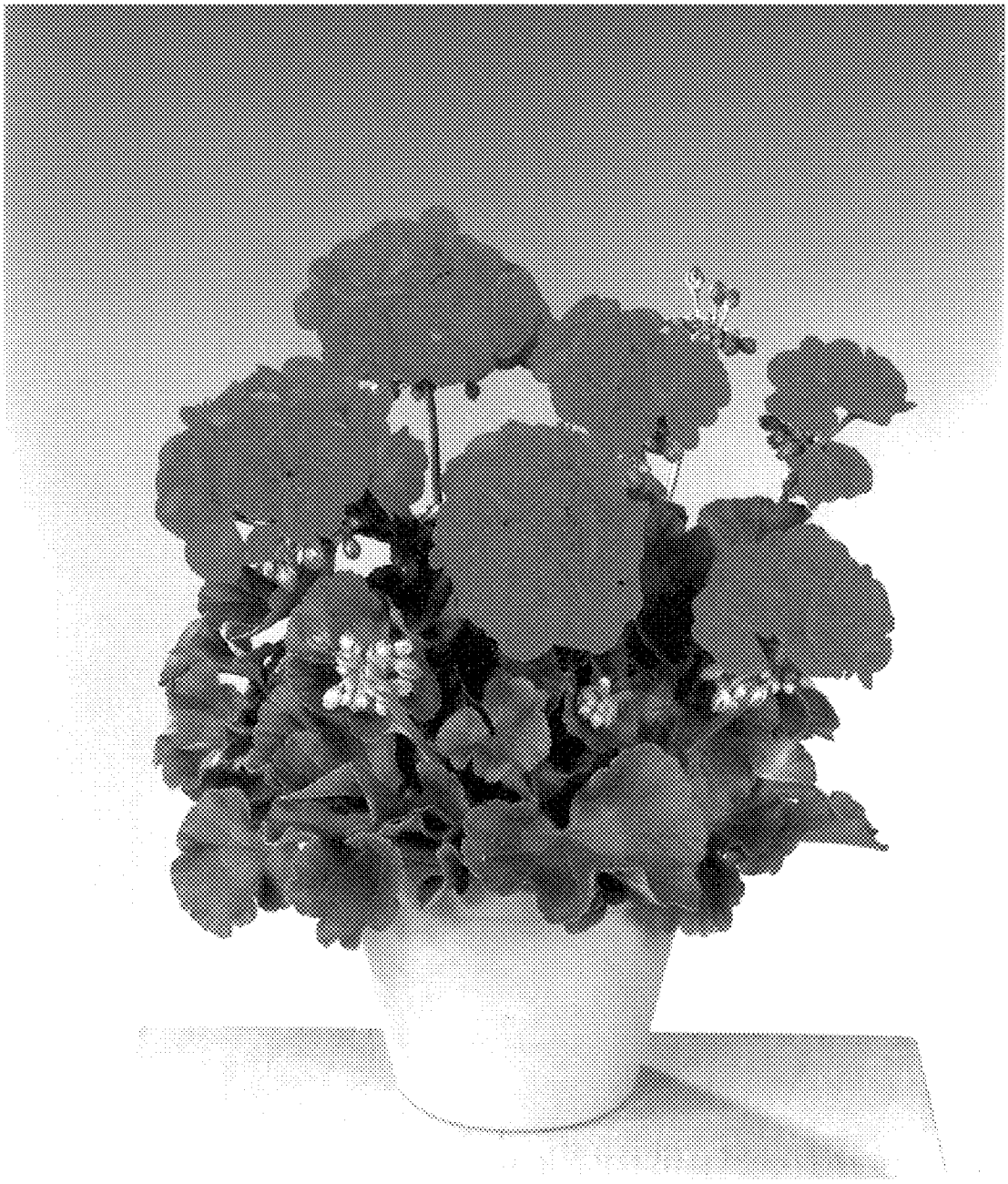

* * * * *